United States Patent [19]

Sato

[11] 4,331,392

[45] May 25, 1982

[54] OPHTHALMOSCOPIC SLIT LAMP

[75] Inventors: Masaru Sato, Tokyo, Japan

[73] Assignee: Tokyo Kogaku Kikai Kabushiki Kaisha, Tokyo, Japan

[21] Appl. No.: 934,205

[22] Filed: Aug. 16, 1978

[30] Foreign Application Priority Data

Aug. 16, 1977 [JP] Japan .................................. 52-97972
Nov. 14, 1977 [JP] Japan ........................... 52-152572[U]
Jun. 16, 1978 [JP] Japan .................................. 53-72959

[51] Int. Cl.³ .............................................. A61B 3/10
[52] U.S. Cl. ......................................... 351/14; 351/7
[58] Field of Search ................. 351/14, 7; 350/35, 36, 350/75, 145, 175 E, 175 ML

[56] References Cited

U.S. PATENT DOCUMENTS 3,533,685 10/1970 Littmann et al. ...................... 351/14
3,652,153 3/1972 Gambs .................................. 351/14
3,749,481 7/1973 Bosack et al. .......................... 351/14
3,830,562 8/1974 McGrann et al. ..................... 351/14
3,925,793 12/1975 Matsumura et al. ................ 351/7 X
4,059,336 11/1977 Hopkins ............................. 350/36 X

OTHER PUBLICATIONS

Topcon Advertisement, *Journal Amer. Optom. Assoc.*, Feb. 1975.

*Primary Examiner*—John K. Corbin
*Assistant Examiner*—Rodney Bovernick
*Attorney, Agent, or Firm*—Stevens, Davis, Miller & Mosher

[57] ABSTRACT

Ophthalmoscopic slit lamp including a slit illumination section, a binocular microscope and a photographing camera. The microscope is mounted on the upper end of a support arm which is swingable about a vertical axis. The camera is also carried by the support arm at a position beneath the microscope so that it does not disturb the operator.

8 Claims, 16 Drawing Figures

OPHTHALMOSCOPIC SLIT LAMP

The present invention relates to ophthalmoscopic slit lamps including an illuminating section for projecting a slit-pattern illumination light to a patient's eye and a binocular microscope section for stereoscopic observation of the illuminated portion of the patient's eye.

Such ophthalmoscopic slit lamps are also equipped with a photographing camera for taking a photograph of the slit-illuminated section of the patient's eye. In conventional slit lamps of this type, inconveniencies have often been encountered in that the photographing camera has been located in such a position where it disturbs the operator of the slit lamp.

Another problem in the conventional slit lamps is the one inherent to the optical system adopted in the microscope section. There are two types of optical systems which can be adopted in the binocular microscope section of the slit lamp, one being the so called Galileo type system having a pair of parallel optical axes through eye lenses and the other the so-called Glino type having a pair of optical axes intersecting each other at a predetermined angle. In the former type, there is a problem of convergence of eyes because an object at a near point must be observed as if it were at an infinitely far point. The problem of eye convergence is of particular importance in slit lamps because the microscopes in the slit lamps are used only for observations of objects at near points.

The latter type of optical system has no problem of eye conversion since it includes a pair of optical axes intersecting each other at a predetermined angle. However, since this type of optical system includes a pair of objective lenses which are respectively adapted to oppose to an object, it is extremely difficult to provide a mechanism which makes it possible to replace the objective lenses for the purpose of changing magnification power. Further, since this type of optical system does not have any portion where the pair of optical axis are parallel with each other, it is impossible to focus light bundles along the optical axes on a single photographing plane. Therefore, it has been required to provide a complicated means in the optical system to take a stereoscopic photograph by means of a single camera.

It is therefore an object of the present invention to provide an ophthalmoscopic slit lamp having a photographing camera mounted in a position where it does not disturb the operator of the slit lamp.

Another object of the present invention is to provide an optical system for the binocular microscope which has no problem of eye conversion but can readily take a stereoscopic photograph by means of a single camera.

A further object of the present invention is to provide an ophthalmoscopic slit lamp which includes simple means for adjusting the width of the slit illumination and the aperture of the illuminating optical system.

According to the present invention, in order to accomplish the above and other objects, there is provided a slit lamp comprising a slit illuminating section including means for illuminating a patient's eye in a pattern of a slit, and a binocular microscope section including support arm means swingable about a vertical axis. The section has an upper end, lens tube means mounted on said support arm means at the upper end thereof, and a binocular optical system having a pair of optical axes and provided in said lens tube means. The optical system includes means for reflecting downwardly parts of light along the optical axes, said lens tube means being formed at a lower portion thereof with aperture means for passing therethrough the parts of light reflected by the reflecting means. The support arm means has camera mount means provided beneath the lens tube means, photographing camera means adapted to be mounted on said camera mount means and having means for introducing into the camera means the parts of light which have passed through the aperture means in the lens tube means.

Preferably, said photographing camera means is mounted on said camera mount means through adapter means which includes reflecting means for directing light from the aperture means to said camera means. Two types of adapter means may be provided for alternative use, one having reflecting means for directing a pair of light bundles reflected at the optical axes simultaneously and parallely toward a photographing film plane in the camera means, and the other having reflecting means for directing only one of the light bundles toward the film plane simultaneously displacing the light bundle toward the center of the film plane.

According to an additional feature of the present invention, the binocular optical system includes objective lens means, a pair of variable magnification optical means having parallely extending optical axes and a pair of image inverting optical means disposed respectively along said optical axes of the variable magnification optical means, said image inverting optical means including reflecting means for reflecting light bundles which have passed along said optical axes in directions inclined oppositely by the same angle with respect to the optical axes to define visual axes which are converged with each other. Such inverting optical means may each be comprised of a first equilateral triangular prism having a rightangle edge and a flat surface opposite to said edge, and a pair of second equilateral triangular prisms each having a rightangle edge placed on said flat surface of the first prism with one of surfaces adjacent to said rightangle edge attached to said flat surface of the first prism, said rightangle edge of one of the second prisms being inclined with respect to the rightangle edge of the first prism in a direction opposite to and by the same angle as the rightangle edge of the other second prism, said inverting optical means being so located that the rightangle edge of the first prism in one of the means is inclined with respect to the associated optical axis by the same angle as and in a direction opposite to the direction of inclination of the corresponding edge of the first prism in the other of the means.

In a preferable aspect of the present invention, the slit illuminating section includes means for adjusting width of illumination slit as well as means for adjusting an aperture of illumination, both of said means being adapted to be controlled by co-axially arranged knob means.

The above and other objects and features of the present invention will become apparent from the following descriptions of preferred embodiments taking reference to the accompanying drawings, in which.

Figures 1, 2:
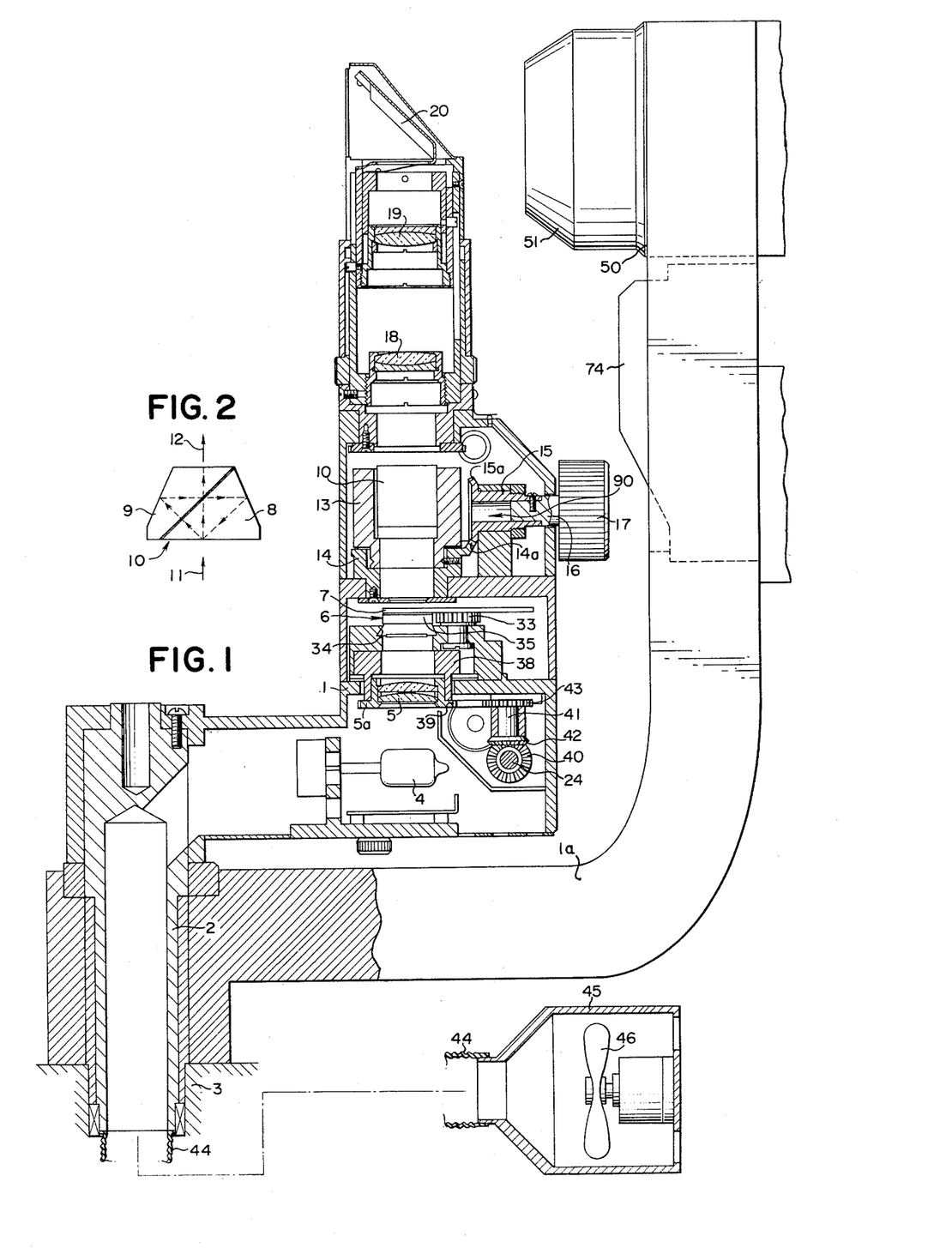
FIG. 1 is a sectional view showing the slit illuminating section of the slit lamp in accordance with one embodiment of the present invention.
FIG. 2 is a view showing an example of image rotating prism assembly adopted in the slit illuminating section.

Referring to the drawings, particularly to FIG. 1, there is shown a slit illuminating section of a slit lamp which comprises an illumination housing 1 mounted by means of a hollow vertical shaft 2 on base 3 for swingable movement about a vertical axis. In the housing 1, there is disposed an illuminating light source in the form of a lamp 4 which projects an illuminating light through a lens 5, a slit mask assembly 6 and an aperture disc 7 to a slit orientation adjusting mechanism 90.

The mechanism 90 includes an image rotating prism assembly 10 which is comprised as shown in FIG. 2 of a first prism 8 and a second prism 9 so that the light from the slit mask assembly 6 is injected along the direction shown by an arrow 11 in FIG. 2 into the first prism 8, reflected in the prisms 8 and 9 as shown by dotted arrows and ejected from the prism 9 coaxially with the incident light as shown by an arrow 12 in FIG. 2. The prism assembly 10 functions to determine the orientation of the slit image of the slit mask assembly 6 about the optical axis in such a manner that, when the prism assembly 10 is rotated about the optical axis defined by the arrows 11 and 12, the slit image is rotated by an angle which is two times as large as the angle of rotation of the prism assembly 10.

The prism assembly 10 is mounted on a prism support member 13 which is in turn mounted on a member 14 rotatable on the housing 1 about an optical axis of the lens 5. The member 14 is formed with bevel gear teeth 14a which are in meshing engagement with cooperating gear teeth 15a formed on a gear member 15 rotatable about a horizontal axis. The gear member 15 has a stem 16 extending rewardly of the housing 1 and having a knob 17 attached thereto. Thus, it will be understood that an actuation of the knob 17 causes the prism assembly 10 to rotate to thereby rotate the slit image correspondingly.

The light which has passed through the prism assembly 10 is then passed through lenses 18 and 19 and reflected by a mirror towards a patient's eye. In the illustrated embodiment, the lens 19 and the mirror 20 are movable as a unit vertically with respect to the housing 1. In order that the slit illumination light be maintained on the patient's eye even when the mirror 20 is vertically moved, means is provided for changing the angle of inclination of the mirror 20 in response to the vertical movement of the mirror 20. An example for such means is shown by Japanese patent publication Sho 40-3518 to which reference is made.

In the illustrated arrangement, the number of teeth 15a on the bevel gear member 15 is one-half of the number of the teeth 14a so that the slit illumination light is rotated by the same angle and in the same direction as the knob 17 rotates. The arrangement is advantageous in that the angle of rotation of the knob 17 is completely coincided with the rotation of the slit illumination so that it is possible to indicate the orientation of the slit by providing an appropriate mark on the knob 17.

Figure 3:
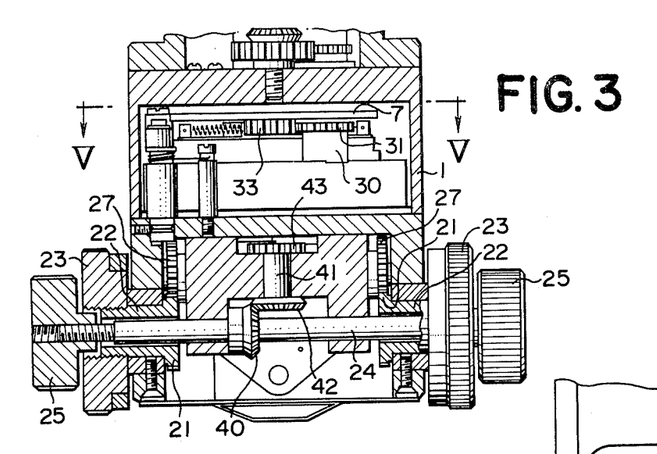
FIG. 3 is a sectional view showing the slit width and aperture adjusting mechanism adopted in the slit illuminating section.

The illustrated arrangement is further characterized by a coaxial arrangement of a slit width adjusting mechanism and an aperture adjusting mechanism. Referring to FIG. 3, the housing 1 is provided at the opposite sides with axially aligned hollow shafts 22 which are rotatably mounted on the housing 1 one on each side. Each of the hollow shaft 22 has an inner end formed with a gear 21 and an outer end to which an aperture adjusting knob 23 is secured. Through the hollow shafts 22, there extends a rotatable shaft 24 which has opposite ends extending beyond the outer ends of the respective hollow shafts 22. A slit width adjusting knob 25 is mounted on each outer end of the rotatable shaft 24.

Figure 4:
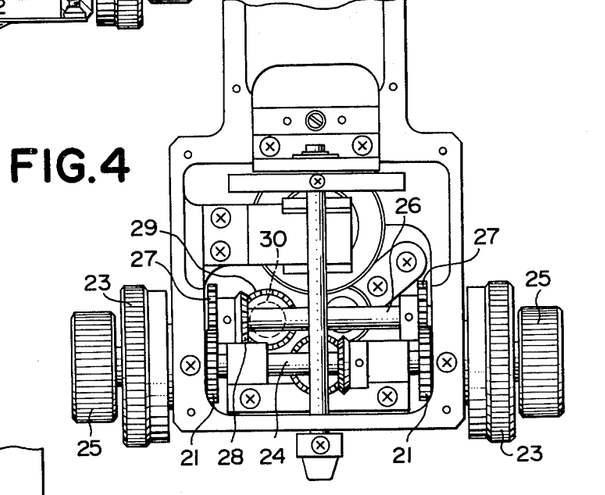
FIG. 4 is a bottom view of the mechanism shown in FIG. 3.

Referring to FIG. 4, it will be noted that the gears 21 are in meshing engagement respectively with gears 27 provided at the opposite ends of a countershaft 26. The shaft 26 is further provided with a bevel gear 28 which engages with a bevel gear 29 provided at the bottom end of a vertical shaft 30. The vertical shaft 30 has a gear 31 which is provided at the upper end thereof and in meshing engagement with a gear 33 provided on the aperture disc 7.

Figure 5:
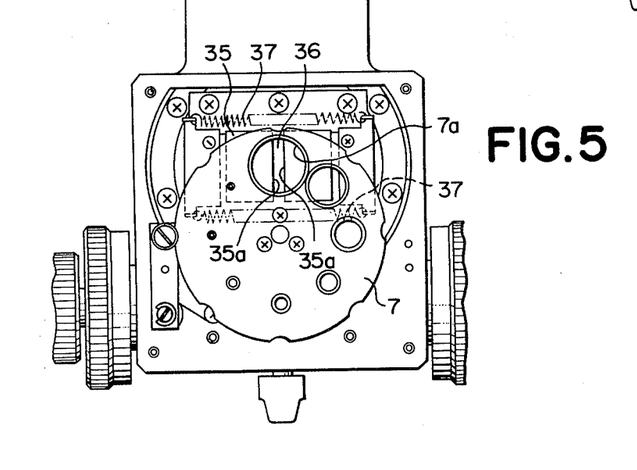
FIG. 5 is a sectional view taken substantially along the line V—V in FIG. 3.

As shown in FIG. 5, the aperture disc 7 has a plurality of apertures 7a of different diameters. An actuation of the knob 23 causes a rotation of the countershaft 26 and the rotation of the countershaft 26 is transmitted through the bevel gears 28 and 29 to the shaft 30 and then through the gears 31 and 33 to the aperture disc 7. Thus, the aperture disc 7 is rotated by means of the knob 23 to locate a selected one of the apertures 7a in the illuminating path.

The slit mesh mechanism 6 includes a pair of slit plates 35 which slide along a dove-tail groove 34 as shown in FIG. 1. A slit gap 36 is defined by opposing edges 35 a of the slit plates 35. The slit plates 35 are biased by means of a spring 37 and forced to move apart from each other by means of a hollow cam 38 which is disposed coaxially with the illuminating optical axis. The cam 38 is secured to a frame 5a of the lens 5 which has gear teeth 39 formed on the external periphery thereof.

The shaft 24 having the knobs 25 secured to the opposite ends thereof is further provided with a bevel gear 40 which is engaged with a bevel gear 42 provided at the bottom end of a vertical shaft 41. The shaft 41 is provided at the upper end with a gear 43 which engages through a counter gear (not shown) with the gear teeth 39 formed on the lens frame 5a. It should therefore be noted that the cam 38 is rotated to adjust the width of the slit 36 by means of the knob 25. The illustrated arrangement is advantageous from the viewpoint of manual adjustment since the knobs for the slit and aperture adjustments are arranged coaxially and the knobs are provided on both sides of the housing 1.

The hollow shaft 2 supporting the housing 1 is connected at the bottom end with a flexible hose 44 which is in turn connected with a fan case 45. In the fan case 45, there is disposed a cooling fan 46 which functions to draw warm air around the lamp 4.

Figures 6, 10:
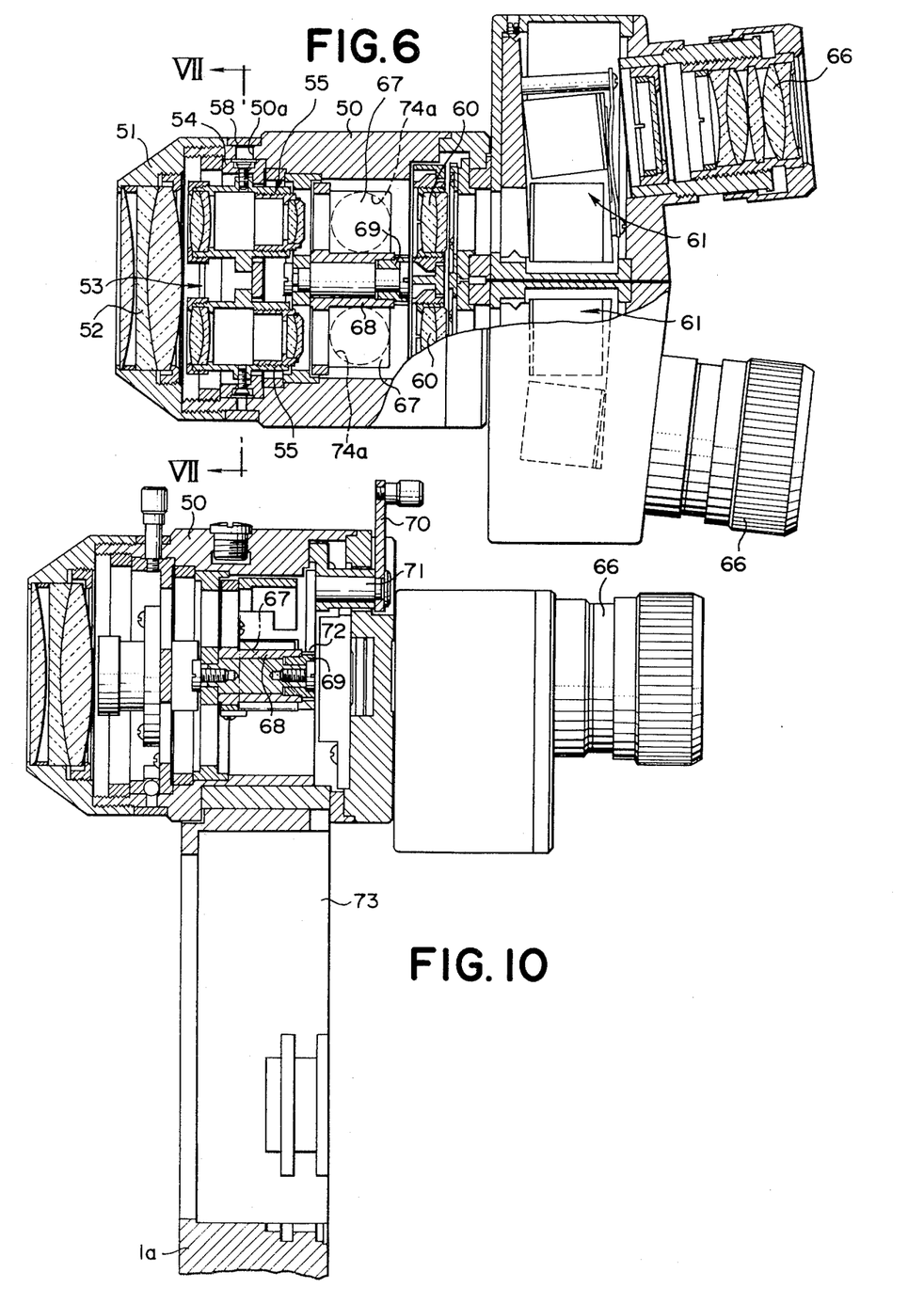
FIG. 6 is a horizontal sectional view of the binocular microscope of the slit lamp in accordance with one embodiment of the present invention.
FIG. 10 is a vertical sectional view of the microscope section shown in FIG. 6.
Figure 7:
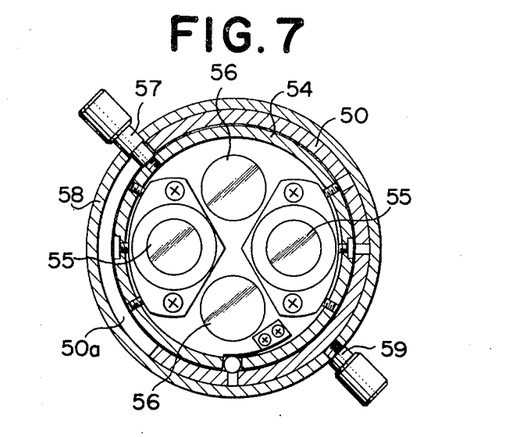
FIG. 7 is a sectional view taken along the line VII—VII in FIG. 6.

The microscope section includes a support arm 1a which is mounted on the hollow shaft 2 for swingable movement about a vertical axis. The arm 1a carries a lens tube 50 at the top end thereof and, as shown in FIG. 6, the lens tube 50 carries at its front end a lens frame 51 on which an objective lens 52 is mounted. Behind the objective lens 52, there is provided a variable magnification lens assembly 53 which defines a pair of parallel optical paths. The lens assembly 53 is comprised of a lens mounting ring 54 which is rotatable about the optical axis of the objective lens 52 and two pairs of lenses 55 and 56 which are disposed as shown in FIG. 7. The ring 54 has an actuating shaft 57 which passes through a circumferential slot 50a formed in the lens tube 50. Outside the lens tube 50, there is mounted a ring 58 which is so arranged that it covers the slot 50a. The ring 58 is secured to the shaft 57 so that it rotates with the lens mounting ring 54. It should of course be noted that one of the lens pairs, for example, the lens pair 56 may be omitted and substituted by simple apertures.

The ring 58 has a knob 59 secured thereto so that the ring 58 and the lens mounting ring 54 can be rotated by the knob 59. The lenses 55 and 56 have different magnification powers and, by rotating the lens mounting ring 54, a selected pair of lenses can be brought into the parallel optical paths which are symmetrical with each other with respect to the optical axis of the objective lens 52. It should be noted that, in the illustrated arrangement, the magnification power is changed through a rotation of the lens mounting ring about the axis of the lens tube 50. This arrangement is advantageous in respect of an axial dimension of the magnification changing mechanism and of appearance over a conventional arrangement wherein the lens mounting ring is rotated about an axis perpendicular to the axis of the lens tube.

Figure 8:
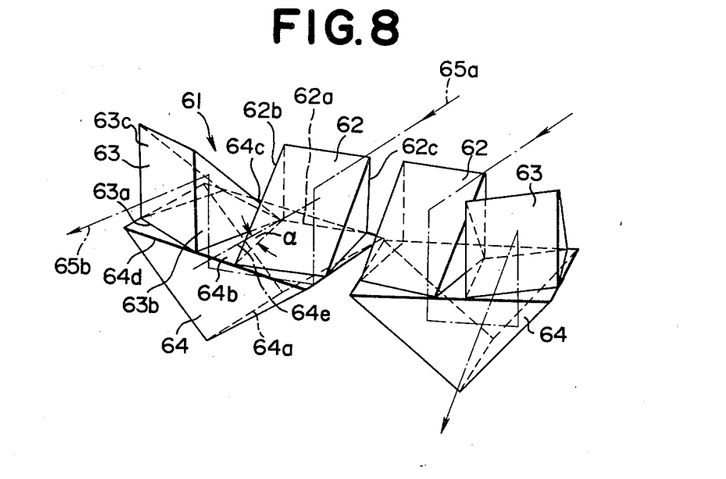
FIG. 8 is a perspective view of image inverting prism asemblies in accordance with one embodiment of the present invention.
Figure 9:
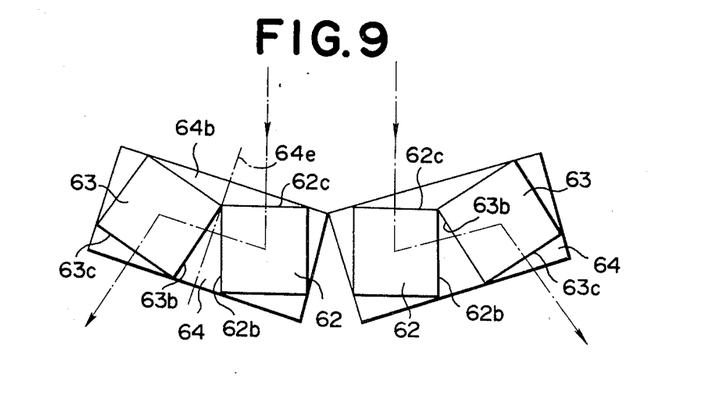
FIG. 9 is a top plan view of the prism assemblies shown in FIG. 8.

Along the optical paths, there are provided behind the lens assembly 53 a pair of focusing lenses 60 and behind the lenses 60 there are provided image inverting prism assemblies 61. As shown in FIGS. 8 and 9, each prism assembly 61 comprises a pair of small equilateral triangular prisms 62 and 63 and a large equilateral triangular prism 64. The prism 64 has a right angle edge 64a and a flat surface 64b opposing to the edge 64a. The prisms 62 and 63 have right angle edges 62a and 63a, respectively, and attached to the prism 64 with surfaces adjacent to the edges 62a and 63a in contact with the surface 64b.

The prism 62 which is the incident side prism is located with the right angle edge 62a adjacent to one side edge 64c of the surface 64 of the prism 64. The prism 63 which is the exit side prism is located with the right angle edge 63a adjacent to the other side edge 64d of the surface 64b. The prism 62 has a side surface 62b which is perpendicular to the edge 62a and inclined by an angle $\alpha$ with respect to a projection 64e of the edge 64a on the surface 64b. The prism 63 has a side surface 63b which is perpendicular to the edge 63a and symmetrical with the surface 62b with respect to the projection 64e. Thus, the right angle edge 62a of the prism 62 is inclined with respect to the edge 64a of the prism 64 or its projection on the surface 64b by the same angle but in the opposite direction as the edge 63a of the prism 63 is.

It should therefore be noted that the incident light 65a perpendicular to the surface 62c adjacent to the right angle edge 62a of the prism 62 is reflected in the prisms 62, 64 and 63 and goes out of the prism assembly perpendicularly through the surface 63c of the prism 63 as shown by an arrow 65b with a divergent angle 2α with respect to the direction of the incident light 65a. The pair of prism assemblies 61 are arranged with the incident surfaces 62c of the prisms 62 located on a common plane and symmetrical with each other with respect to the optical axis of the objective lens 52. Thus, the exit lights 65b from the prism assemblies 61 have the aforementioned divergent angles with respect optical axis of the objective lens 52. As shown in FIG. 6, eyepieces 66 are disposed along the exit paths of the prism assemblies.

Between the lens assembly 53 and each lens 60, there is provided a prism 67 which functions as a half-transparent mirror so that a part of the light from the lens assembly 53 is reflected downwardly. The prisms 67 are mounted on a shaft 68 which is rotatable about the optical axis of the objective lens 52 as shown in FIGS. 6 and 10. The shaft 68 is provided at the rear end with a gear 69 which meshes with a sector gear 72 provided on a rotatable shaft 71. A handle 70 is provided for rotating the shaft 71 so that the shaft 68 can be rotated by means of the handle 70 through the gears 72 and 69 by 90° to retract the prisms 67 from the optical paths of the microscope.

The lens tube 50 is formed at the lower portion with apertures 74a for passing therethrough the light reflected by the prisms 67. Beneath the lens tube 50, the support arm 1a is formed with a camera frame 73 for mounting an adapter for a photographing camera.

Figures 11, 12:
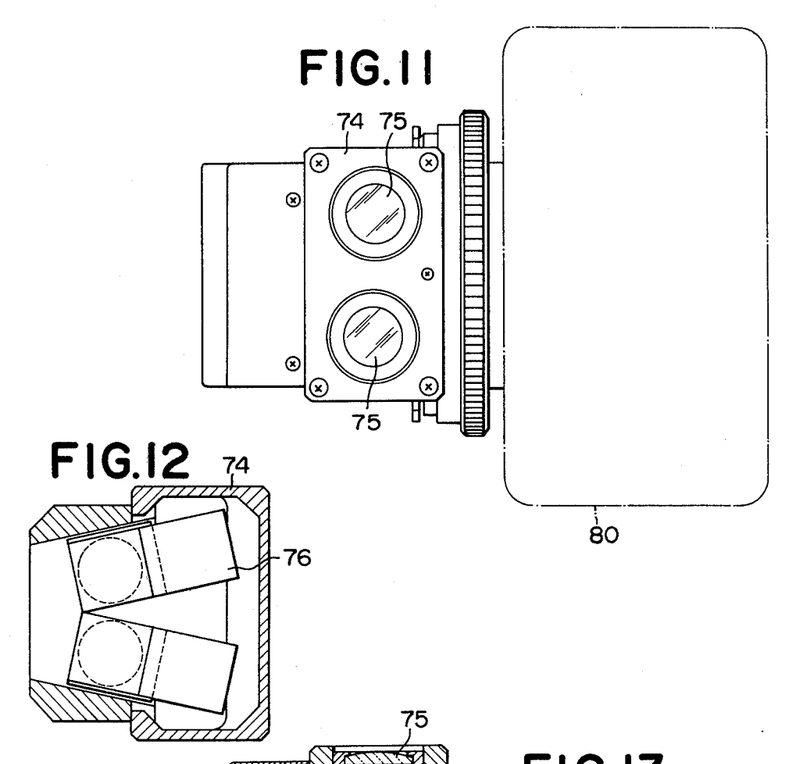
FIG. 11 is a plan view of a stereoscopic camera adapter for mounting a photographing camera on the microscope section.
FIG. 12 is a horizontal sectional view of the adapter shown in FIG. 11.
Figure 13:
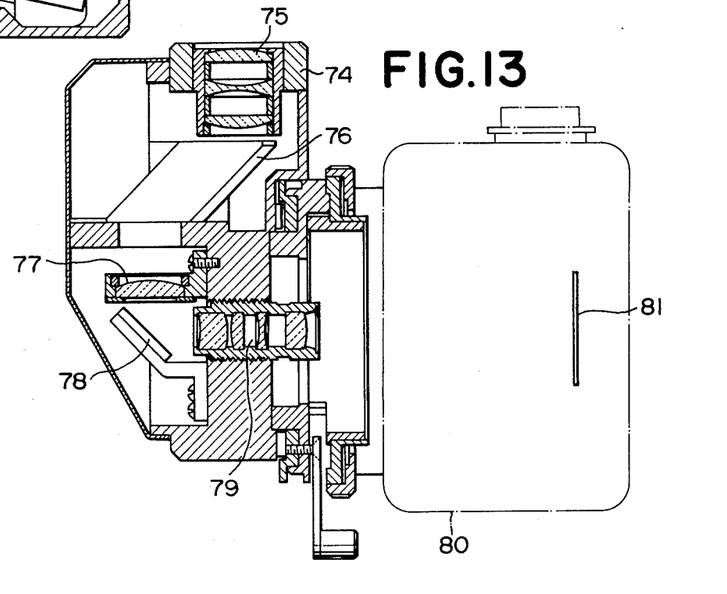
FIG. 13 is a vertical sectional view of the adapter shown in FIGS. 11 and 12.

Referring to FIGS. 11 through 13, there is shown an example of such camera adapter for stereoscopic photographing. The adapter comprises a rectangular housing 74 adapted to be fitted to the camera carrier frame 73. At the upper portion of the housing 74, there are mounted a pair of relay lenses 74 which are positioned to oppose to the apertures 74 formed in the lower portion of the lens tube 50. Beneath the relay lenses 75, there are provided a pair of prisms 76 which function to displace a pair of light bundles through the lenses 75 laterally inwardly toward each other and thereafter direct them downwardly. The light bundles are then passed through a field lens 77 and reflected rearwardly by means of a mirror 78. The light bundles are thereafter passed through a lens 79 and focused on a film 81 in a photographing camera 80 which may be mounted on the housing through a suitable known mechanism.

Figure 14:
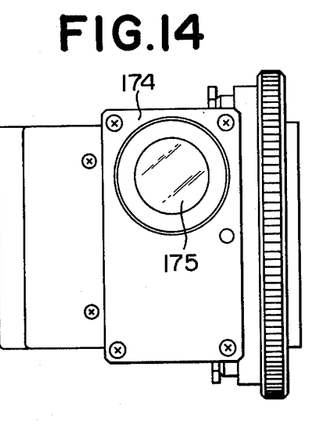
FIG. 14 is a plan view of a single path camera adapter.
Figure 15:
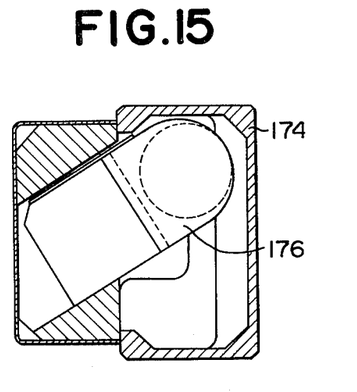
FIG. 15 is a horizontal sectional view of the camera adpater shown in FIG. 14.
Figure 16:
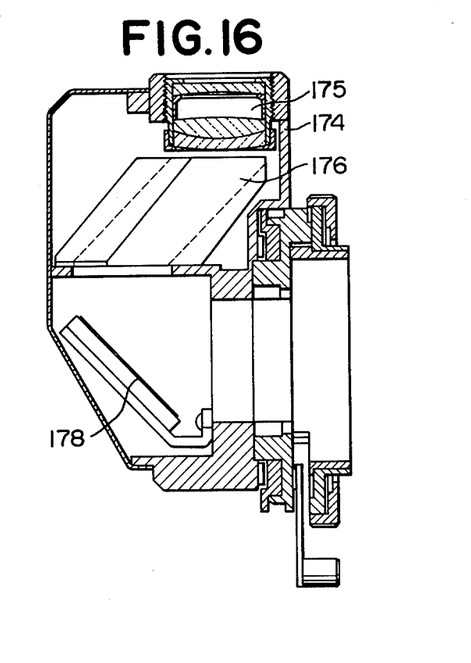
FIG. 16 is a vertical section of the camera adapter shown in FIGS. 14 and 15.

Referring to FIGS. 14 through 16, there is shown an example of a camera adapter for taking a single picture. The adapter comprises a rectangular housing 174 which is adapted to be fitted to the camera carrier frame 73. The housing 174 is provided at the upper portion thereof with a lens 175 which is located at a position opposing to one of the apertures 74a in the lens tube 50. Beneath the lens 175, there is provided a prism 176 which functions to shift the light from the lens 175 toward the center of the housing 174. The light from the prism 176 is reflected by a mirror 178 toward the camera.

According to the arrangement described above, the light which has passed through the objective lens is divided into two parallel light bundles which are symmetrical with each other and portions of the light bundles are downwardly reflected by the half-transparent elements. The reflected light portions are then directed to the photographing camera which is carried by the support arm for the microscope. Since the camera is positioned beneath the microscope and carried by the support arm, it is possible to locate the camera in such a manner that it does not disturb the operator.

The optical system of the microscope as shown in FIG. 6 is advantageous in that the light which has passed through the objective lens is divided into two parallel bundles and then directed to the eyepieces 66 with a divergent angle so that there is no problem of eye convergence. Further, since the magnification changing lens assembly can be positioned in such a portion where the two divided light bundles are parallel with each other, it is possible to simplify the magnification changing mechanism.

The invention has thus been shown and described with reference to specific arrangements, however, it should be noted that the invention is in no way limited to the details of the illustrated structures but changes and modifications may be made without departing from the scope of the appended claims.

I claim:

1. Ophthalmoscopic slit lamp comprising a slit illuminating section including means for illuminating a patient's eye in a pattern of a slit, and a binocular microscope section including support arm means, means for mounting the lower end of said support arm means for swingable movement about a vertical axis, lens tube means mounted on said support arm means at the upper end thereof, and a binocular optical system having objective lens means at one end of said lens tube means and a pair of optical axes in said lens tube means leading to binocular viewing eyepieces at the other end of said lens tube, said binocular optical system including, a pair of variable magnification optical means having parallelly extending optical axes and a pair of image inverting optical means disposed respectively along said optical axes of the variable magnification optical means, prism means in said lens tube near said other end for reflecting said pair of optical axes into said eyepieces, said optical system including means in said lens tube between said objective lens and said prism means for reflecting downwardly part of the light along the optical axes, said lens tube means having aperture means at a lower portion thereof for passing therethrough part of the light reflected by the reflecting means, camera mount means on said support arm means between said mounting means and said lens tube means, photographing camera means adapted to be mounted on said camera mount means with a photographing film held in a vertical plane through adapter means which includes second reflecting means for directing light from the aperture means to the camera means.

2. Slit lamp in accordance with claim 1 in which said second reflecting means includes a pair of reflecting elements for directing a pair of light bundles reflected at the optical axes simultaneously and parallelly toward the photographing film plane in the camera means.

3. Slit lamp in accordance with claim 1 in which said second reflecting means includes a reflecting element for directing only one of a pair of light bundles reflected at the optical axes toward the photographing film plane and simultaneously displacing the light bundle toward the center of the film plane.

4. Slit lamp in accordance with claim 1 in which said image inverting optical means includes reflecting means for reflecting light bundles which have passed along said optical axes in directions inclined oppositely by the same angle with respect to the optical axes to define visual axes which are converged with each other.

5. Slit lamp in accordance with claim 4 in which each of said inverting optical means comprises a first equilateral triangular prism having a rightangle edge and a flat surface opposite to said edge, and a pair of second equilateral triangular prisms each having a rightangle edge placed on said flat surface of the first prism with one of said surfaces adjacent to said rightangle edge attached to said flat surface of the first prism, said rightangle edge of one of the second prisms being inclined with respect to the rightangle edge of the first prism in a direction opposite to and by the same angle as the rightangle edge of the other second prism, said inverting optical means being so located that the rightangle edge of the first prism in one of the means is inclined with respect to the associated optical axis by the same angle as and in a direction opposite to the direction of inclination of the corresponding edge of the first prism in the other of the means.

6. Slit lamp in accordance with claim 1 in which said slit illuminating section includes means for adjusting the width of the illumination slit as well as means for adjusting the aperture of illumination, coaxial knob means connected to control both of said adjusting means.

7. Slit lamp is accordance with claim 4 in which said variable magnification optical means includes lens mounting frame means which is rotatable about an optical axis of the objective lens means and carries magnification lens means which is adapted to be selectively positioned in said parallelly extending optical axes.

8. Slit lamp according to claim 1, in which said adapter means is removeably attached to the camera mount means.

* * * * *